US011690821B2

(12) United States Patent
Missling et al.

(10) Patent No.: US 11,690,821 B2
(45) Date of Patent: *Jul. 4, 2023

(54) A19-144, A2-73 AND CERTAIN ANTICHOLINESTERASE INHIBITOR COMPOSITIONS AND METHOD FOR ANTI-SEIZURE THERAPY

(71) Applicant: ANAVEX LIFE SCIENCES CORP., New York, NY (US)

(72) Inventors: Christopher U. Missling, New York, NY (US); Cameron Durrant, Califon, NJ (US)

(73) Assignee: ANAVEX LIFE SCIENCES CORP., New York, NY (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/080,471

(22) Filed: Oct. 26, 2020

(65) Prior Publication Data

US 2021/0046038 A1  Feb. 18, 2021

Related U.S. Application Data

(60) Continuation of application No. 16/601,323, filed on Oct. 14, 2019, now Pat. No. 10,813,907, which is a division of application No. 15/571,877, filed as application No. PCT/US2015/056172 on Oct. 19, 2015, now Pat. No. 10,441,563.

(60) Provisional application No. 62/065,833, filed on Oct. 20, 2014.

(51) Int. Cl.
| | |
|---|---|
| *A61K 31/341* | (2006.01) |
| *A61K 31/4015* | (2006.01) |
| *A61K 31/445* | (2006.01) |
| *A61K 31/55* | (2006.01) |
| *A61P 25/08* | (2006.01) |
| *C07D 307/14* | (2006.01) |
| *A61K 31/27* | (2006.01) |
| *A61K 31/165* | (2006.01) |
| *A61K 45/06* | (2006.01) |

(52) U.S. Cl.
CPC .......... *A61K 31/341* (2013.01); *A61K 31/165* (2013.01); *A61K 31/27* (2013.01); *A61K 31/4015* (2013.01); *A61K 31/445* (2013.01); *A61K 31/55* (2013.01); *A61K 45/06* (2013.01); *A61P 25/08* (2018.01); *C07D 307/14* (2013.01)

(58) Field of Classification Search
CPC .... A61K 31/341; A61K 31/165; A61K 31/27; A61K 31/4015; A61K 31/445; A61K 31/55; A61K 45/06; A61P 25/08
See application file for complete search history.

(56) References Cited

U.S. PATENT DOCUMENTS

| | | |
|---|---|---|
| 2006/0252745 A1 | 11/2006 | Almeida et al. |
| 2007/0049576 A1 | 3/2007 | Barlow et al. |
| 2010/0069484 A1 | 3/2010 | Vamvakides et al. |
| 2010/0297181 A1 | 11/2010 | Hanada et al. |
| 2014/0288058 A1 | 9/2014 | de Almeida et al. |
| 2014/0296211 A1 | 10/2014 | Vamvakides et al. |

FOREIGN PATENT DOCUMENTS

| | | | |
|---|---|---|---|
| WO | WO 97/30983 | * | 8/1997 |
| WO | 2007025177 A2 | | 3/2007 |
| WO | 2008087458 A2 | | 7/2008 |
| WO | 2009082039 A1 | | 7/2009 |
| WO | 2013008044 A1 | | 1/2013 |
| WO | 2014155138 A1 | | 10/2014 |

OTHER PUBLICATIONS

International Search Report and Written Opinion dated Nov. 21, 2015 in corresponding International Application No. PCT/US15/56172.
Extended European Search Report for EP 15852696 dated Mar. 14, 2018, 9 pages.
Knutsen, L et al., Worldwide Discovery Research, Cephalon Inc., West Chester, PA, USA; Comprehensive Medicinal Chemistry II Section 6 11, copyright 2007,20 pages.
Vamvakides, A, "Effects anticonvulsivant et anti-immobilite (nage forecee) de la tetrahydro-N, N-dimethyl-2, 2-diphenyl-3-furanemethanamine," Ann. Pharm, Fr. 2002, 60, 88-92.
Pathan, S. et al., "Insights into novel three 'D's of epilepsy treatment: drugs, delivery systems and devices," Drug Discovery Today, vol. 15, Nos. 17/18, Sep. 2010, 16 pages.
International Preliminary Report on Patentability for International Application No. PCT/US2015/056172 dated May 4, 2017, 5 pages.

* cited by examiner

*Primary Examiner* — Sahar Javanmard
(74) *Attorney, Agent, or Firm* — Polsinelli PC; Tara A. Nealey

(57) ABSTRACT

This invention concerns a dosage form comprising a therapeutically effective amount of A19-144 or A2-73 and a therapeutically effective amount of at least one AED. This invention further encompasses a method of treating a subject in need of such treatment comprising administering a therapeutically effective amount of A19-144 or A2-73 in conjunction with any therapeutically effective amount of an AED.

20 Claims, 1 Drawing Sheet

A19-144, A2-73 AND CERTAIN ANTICHOLINESTERASE INHIBITOR COMPOSITIONS AND METHOD FOR ANTI-SEIZURE THERAPY

CROSS REFERENCE TO RELATED APPLICATIONS

This application is a continuation of U.S. patent application Ser. No. 16/601,323, filed Oct. 14, 2019, which is a divisional of U.S. patent application Ser. No. 15/571,877, filed Nov. 6, 2017, which is the 35 U.S.C. 371 National Stage of International Application Number PCT/US2015/056172, filed Oct. 19, 2015, which claims the priority of U.S. Provisional Application No. 62/065,833, filed Oct. 20, 2014, the entire disclosure of each is hereby incorporated by reference in its entirety.

FIELD OF THE INVENTION

This invention concerns a dosage form comprising a therapeutically effective amount of A19-144, alone and in combination with at least one anti-epilepsy drug (AED) in a therapeutically effective anti-seizure amount. Particular reference is made to seizures arising from epilepsy. This invention further concerns a dosage form comprising a therapeutically effective amount of A2-73, alone and in combination with at least one anti-epilepsy drug (AED) in a therapeutically effective anti-seizure amount.

BACKGROUND 1-(2,2-diphenyltetrahydrofuran-3-yl)-N-methylmethanamine hydrochloride (ANAVEX19-144, or A19-144) is a compound which is believed to bind to muscarinic acetylcholine and sigma-1 receptors with affinities in the low micromolar range. It has been reported that A19-144 showed neuroprotective potential against amyloid toxicity in mice. Anavex 2-73 (also termed A2-73) has a systematic name 1-(2,2-diphenyltetrahydrofuran-3-yl)-N,N-dimethylmethanamine hydrochloride and displays similar activity.

In particular, A19-144 has been reported as attenuating oxidative stress, caspases induction, cellular loss and learning and memory deficits observed in mice one week after the icy injection of an oligomeric preparation of amyloid p25-35 peptide ($A\beta_{25-35}$) (Villard et al., J Psychopharmacol 2011). More recently, it has been reported that A19-144 blocked the $A\beta_{25-35}$-induced P-Akt decrease and P-GSK-3β increase, indicating activation of the PI3K neuroprotective pathway (Lahmy et al., Neuropsychopharmacology, 2013). In the dose-range tested, A19-144 attenuated the hyperphosphorylation of Tau on physiological epitopes (AT-8 antibody clone) and on pathological epitopes (AT-100 clone). ANAVEX2-73 also has been reported decreasing the $A\beta_{25-35}$-induced endogenous $A\beta_{1-42}$ seeding.

A series of aminotetrahydrofuran compounds have been reported as exhibiting anti-amnesic, anticonvulsant, antidepressant and neuroprotective activities.[1-4] Among them, tetrahydro-N, N-dimethyl-2,2-diphenyl-3-furanmethanam ine hydrochloride (ANAVEX2-73) is a mixed muscarinic/$\sigma_1$ protein profile, but with better selectivity for the $\sigma_1$ subtype as compared with $\sigma_2$ sites.[1] Reported binding analyses showed an $IC_{50}=860$ nM for $\sigma_1$ and no affinity for $\sigma_2$ sites. Moreover, the screening profile showed micromolar affinities for muscarinic M1-M4 receptors ($IC_{50}=3.3-5.2$ μM), sodium channel site 2 ($IC_{50}=5.1$ μM), and NMDA receptors ($IC_{50}=8.0$ μM).

Epilepsy is a chronic neurological disorder presenting a wide spectrum of diseases that affect approximately 50 million people worldwide. Neuronal activity is a prerequisite for proper brain function. However, disturbing the excitatory--inhibitory equilibrium of neuronal activity may induce epileptic seizures. These epileptic seizures can be grouped into two basic categories of (i) partial, and (ii) generalized. Without being bound by any particular theory, partial seizures originate in specific brain regions and remain localized—most commonly the temporal lobes (containing the hippocampus), whereas generalized seizures appear in the entire forebrain as a secondary generalization of a partial seizure. The International League Against Epilepsy further classified partial seizures, separating them into simple and complex, depending on the presence or the impairment of a consciousness state (Dreifuss et al., 1981). The league also categorized generalized seizures into numerous clinical seizure types, some examples of which are outlined below:

"Absence seizures" occur frequently, having a sudden onset and interruption of ongoing activities. Additionally, speech is slowed or impeded with seizures lasting only a few seconds;

"Tonic-clonic seizures," often known as "grand mal", are the most frequently encountered of the generalized seizures (Dreifuss et al., 1981). This generalized seizure type has two stages: tonic muscle contractions which then give way to a clonic stage of convulsive movements. The patient remains unconscious throughout the seizure and for a variable period of time afterwards ; and "Atonic seizures," known as "drop attacks", are the result of sudden loss of muscle tone to either a specific muscle, muscle group or all muscles in the body.

Reference is also made to other antiepileptic drugs. Note is made of Acetazolamide; Benzodiazepines (e.g., Clonazepam/Klonopin®, Clorazepate/Tranxene®, diazepam/Valium®, lorazepam/Ativan®, midazolam); Carbamazepine (Tegretol®/Carbatrol®); Chlordiazepoxide; Clobazam; Cortiosteroids; Eslicarbazepine/ Eslicarbazepine acetate; Ethosuximide (Zarontin®); Ethotoin; Felbamate; Lacosamide (Vimpat®); Lamotrigine (Lam ictal®); Levetiracetam (Keppra®); Mephyntoin; Mephobarbitol; Methsuxamide; Oxcarbazepine (Trileptal®); Paramethadione; Perampanel (Fycompa); Phenacemide; Phenobarbital; Phensuxamide; Phenytoin (Dilantin®); Pregabalin (Lyrica®); Primidone (Mysoline®); Progabide; Rufinamide; Stiripentol; Sulthiame; Tiagabine (Gabitril®); Topiramate (e.g., Topamax®); Tremethadione; Valproate (Depakote®); Vigabatrin; and, Zonisamide (Zonegram®).

For convenience, these drugs as well as donepezil, memantine, galantamine, and ribastigimine will be collectively referred to as "anti-epilepsy drugs" or "AED's."

REFERENCES

Reference is made to the following publications, the teachings of which are incorporated by reference in their entirety as are all documents cited herein.

1. Vamvakides (2002) Ann Pharm Fr 60:88-92;
2. Vamvakides (2002) Ann Pharm Fr 60:415-22;
3. Espallergues et al. (2007) Br J Pharmacol 152:267-79;
4. Villard et al (2009) Neuropsychopharmacology 34:1552-66;
5. Maurice et al. (1996) Brain Res 706:181-93;
6. Zussy et al. (2011) Am J Pathol 179:315-34;
7. Hayashi & Su (2007) Cell 131:596-610;
8. Su et al. (2010) Trends Pharmacol Sci 31:557-566;
9. Meunier et al. (2006) Br J Pharmacol 149:998-1012.
10. European Patent Application No. 08 702 158.0, "New Sigma-Receptor Ligands with Anti-Apoptotic and/or Pro-Apoptotic Properties Over Cellular Biochemical Mechanisms, With Neuroprotective, Anti-Cancer, Anti-Metastic and Anti-(Chronic) Inflammatory Action (also, U.S. Ser. No. 12/522,761).
11. U.S. Ser. No. 13/201,271, "Sigma(S)-Receptor Ligands With Anti-Apoptotic and/or Pro-Apoptotic Properties."
12. Dovey et al., "Functional gamma-secretase inhibitors reduce beta-amyloid peptide levels in brain", J Neurochem. 2001 January; 76(1):173-81
13. Motamedi, G K et al., "Antiepileptic drugs and memory", Epilepsy Behav. 2004 August; 5(4):435-9.
14. Michelle Price et al.,"Antiepileptic drugs for the primary and secondary prevention of seizures after intracranial venous thrombosis", Intervention Review, Cochrane Epilepsy Group Published Online: 2 AUG 2014, Assessed as up-to-date: 12 AUG 2013, DOI: 10.1002/14651858. CD005501.pub3
15. Vajda F J et al., "The efficacy of the newer antiepileptic drugs in controlling seizures in pregnancy", Epilepsia. 2014 August; 55(8):1229-34, doi: 10.1111/epi.12711. Epub 2014 Jul. 3.
16. Smith, B N, "Prophylaxis for post-traumatic epilepsy: can your kinase do that?", Epilepsy Curr. 2014 January; 14(1):38-40, doi: 10.5698/1535-7597-14.1.38.
17. Sykes L et al., "Antiepileptic drugs for the primary and secondary prevention of seizures after stroke", Cochrane Database Syst Rev. 2014 Jan. 24; 1:CD005398, doi: 10.1002/14651858. CD005398.pub3.
18. Baslow M H, "N-acetylaspartate in the vertebrate brain: metabolism and function", Neurochem Res. 2003 June; 28(6):941-53.

SUMMARY OF THE INVENTION

STRUCTURE 1

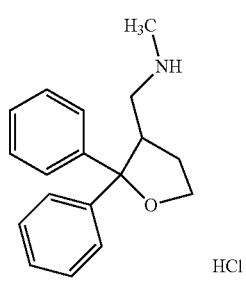

1-(2,2-diphenyltetrahydrofuran-3-yl)-N-methylmethanamine hydrochloride

Anavex19-144

Structure 1 has the systematic name 1-(2,2-diphenyltetrahydrofuran-3-yl)-N-methylmethanamine hydrochloride.

STRUCTURE 2

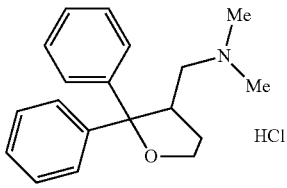

1-(2,2-diphenyltetrahydrofuran-3-yl)-N,N-dimethyl-methanamine hydrochloride

Anavex2-73

Structure 2 has the systematic name 1-(2,2-diphenyltetrahydrofuran-3-yl)-N,N-dimethylmethanamine hydrochloride.

The invention concerns dosages form comprising a therapeutically effective amount of A19-144 and A2-73 and a therapeutically effective anti-seizure amount of at least one AED. For convenience A19-144 and A2-73 will, at times, be collectively referred to herein as "A19/2."

It is a particular advantage of the combination of A19/2 and AED is that, in combination with A19-144 or A2-73, sub-MED doses of AED are therapeutically effective. AED's are implicated in memory loss in subjects taking AED's. Lower AED doses result is absent or lessened memory loss or memory impairment.

In some embodiments, the AED is donepezil, with reference to donepezil at from about 0.5 mg to about 23 mg, and particularly from about 0.5 mg to less than about 5 mg, and more particularly from about 1 to about 3.5 mg. With the synergistic effect in combination with A19-144 or A2-73, doses below 0.5 mg are effective.

In other embodiments the AED is galantamine, and particularly from about 0.5 mg to about 20 mg. With the synergistic effect in combination with A19/2 doses below 8 mg /day are therapeutically effective. Particular note is made of dosing at 6 mg/day. Doses are usefully delivered in about 2 doses.

Attention is drawn to a dosage form wherein said AED is rivastagmine, and particularly from about 0.5 mg to about 20 mg. With the synergistic effect in combination with A19/2, doses below 3 mg /day are therapeutically effective. Particular note is made of dosing at 2 mg/day. Doses are usefully delivered in about 2 doses (morning and evening).

Further attention is drawn to the dosage form an AED is memantine, with particular reference to an anti-seizure amount of from about 0.5 mg to about 30 mg. With the synergistic effect in combination with A19/2, doses below 0.5 mg/day are therapeutically effective. Particular note is made of dosing at 0.4 mg/day.

This invention further includes a therapeutic method of anti-seizure therapy in a subject exhibiting seizure activity with particular reference to epilepsy. Comprising a therapeutically effective dose of A19/2 in conjunction with a therapeutically effective dose of at least one AED. Note is further made of co-timely administration of said therapeutically effective amount of A19-144 in conjunction with a therapeutically effective amount of at least one AED dose selected from the group consisting of Acetazolamide; Benzodiazepines (e.g., Clonazepam/Klonopin®, Clorazepate/Tranxene®, diazepam/Valium®, lorazepam/Ativan®, midazolam); Carbamazepine (Tegretol®/Carbatrol®); Chlordiazepoxide; Clobazam; Cortiosteroids; Eslicarbazepine/ Eslicarbazepine acetate; Ethosuximide (Zarontin®); Ethotoin; Felbamate; Lacosamide (Vimpat®); Lamotrigine (Lam ictal®); Levetiracetam (Keppra®); Mephyntoin; Mephobarbitol; Methsuximide; Oxcarbazepine (Trileptal®); Paramethadione; Perampanel (Fycom pa); Phenacemide; Phenobarbital; Phensuxamide; Phenytoin (Dilantin®); Pregabalin (Lyrica®); Prim idone (Mysoline®); Progabide; Rufinamide; Stiripentol; Sulthiame; Tiagabine (Gabitril®); Topiramate (e.g., Topamax®); Tremethadione; Valproate (Depakote®); Vigabatrin; and, Zonisamide (Zonegram®) as well as donepezil, memantine, galantamine, and rivastigmine. Particular reference is made to donepezil dosed at from about 0.5 mg to about 23 mg, and particularly from about 0.5 mg to less than about 5 mg, and more particularly from about 1 to about 3.5 mg.

Note is made of the following sub-MED doses:

Acetazolamide, less than about 8 mg/kg/day;
Clonazepam/Klonopin®, less than about 1.5 mg/day for adults and for children up to 10 years of age or 30 kg of body weight, doses of less than about 0.01 mg/kg/day;
Clorazepate/Tranxene®, less than about 30 (mg);
Lorazepam/Ativan®, less than about 0.1 mg/kg;
Midazolam (intranasal midazolam in children) less than about 0.2 mg/kg;
Carbamazepine (Tegretol®/Carbatrol®), less than about 7.5 mg/day;
Diazepam /Valium®, less than about 0.2 mg/kg;
Chlordiazepoxide, less than about 30 mg/day;
Clobazam, for body weight 30 kg or less, less than about 5 mg/day and for body weight 30 kg or more, less than about 10 mg/day;
Hydrocortisone, less than about 5 mg/kg/day;
Eslicarbazepine/ Eslicarbazepine acetate, less than about 800 mg/day;
Ethosuximide (Zarontin®), less than about 250 mg daily every 4-7 days;
Ethotoin, less than about 2g daily;
Felbamate, for adults, less than about 1200 mg/day, for children 2-14yrs, less than about 15 mg/kg/day;
Lacosamide (Vimpat®), less than about 50 mg twice daily.
Lamotrigine (Lamictal®), less than about 25 mg/day;
Levetiracetam (Keppra®); less than about 1000 mg/day;
Mephyntoin, less than about 200 mg/day;
Mephobarbitol; less than about 400 mg/day;
Methsuxamide, less than about 250 mg daily every 4-7 days;
Oxcarbazepine (Trileptal®); less than about 600 mg/day;
Paramethadione; less than about 150 mg/day;
Perampanel (Fycompa), less than about 2 mg/day;
Phenacemide, less than about 500 milligrams three times a day;
Phenobarbital, establish a serum level of less than about 10 µg/mL;
Phensuxamide, less than about 0.5 g b.i.d;
Phenytoin (Dilantin®), less than about 100 mg a day;
Pregabalin (Lyrica®), less than about 75 mg 2 times a day;
Primidone (Mysoline®); a dose of less than about 10 mg/kg/day;
Progabide, daily dose of less than about 2100 mg;
Rufinamide, less than about 400 mg/day;
Stiripentol, less than about 250 mg twice a day;
Sulthiame, less than about 100 mg/day;
Tiagabine (Gabitril®), less than about 4 mg/ day;
Topiramate (e.g., Topamax®), less than about 25 mg/day;
Tremethadione, less than about 900 mg/day;
Valproate (Depakote®), less than about 10 mg/kg;
Vigabatrin, less than about 50 mg/kg/day and,
Zonisamide (Zonegram®), less than about 100 mg once a day.

DETAILED DESCRIPTION OF THE INVENTION

Figure 1:
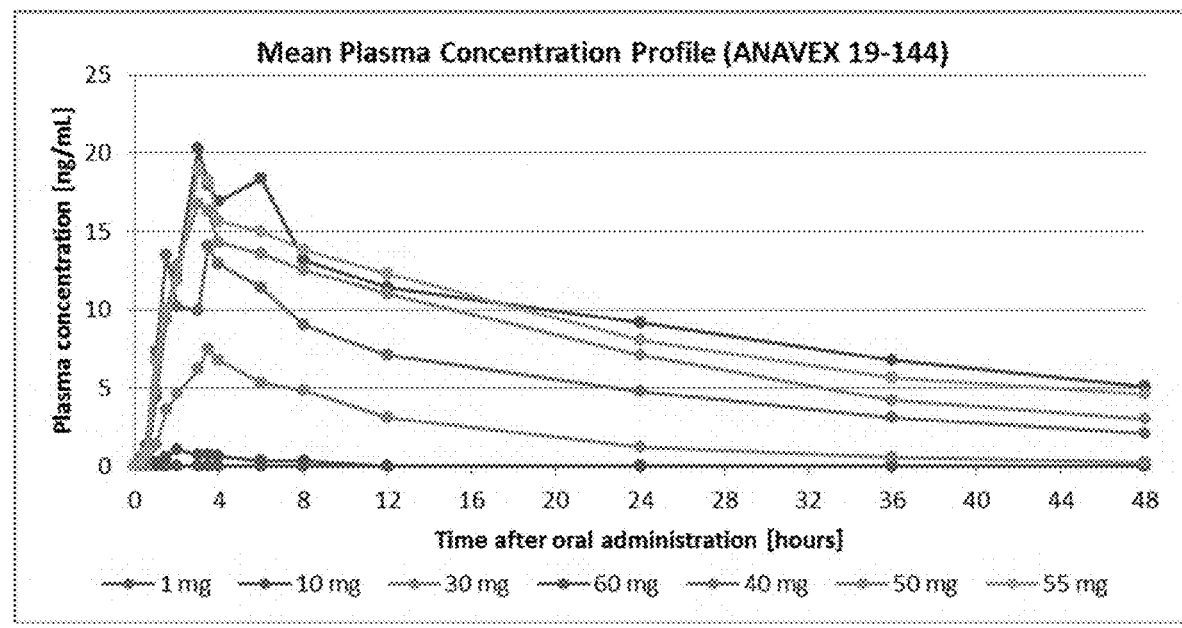
FIG. 1 shows main metabolite ANAVEX19-144: Mean $C_{max}$ values and mean terminal elimination half-life $t_{1/2}$ of AV19-144 show a dose dependent increase across the 10 to 60 mg AV2-73 dose steps (with the exception of the 40 mg step) and ranged from 1.31 to 22.28 ng/ml and 8.56 hours to 28.74 hours, respectively.
Figure 2:
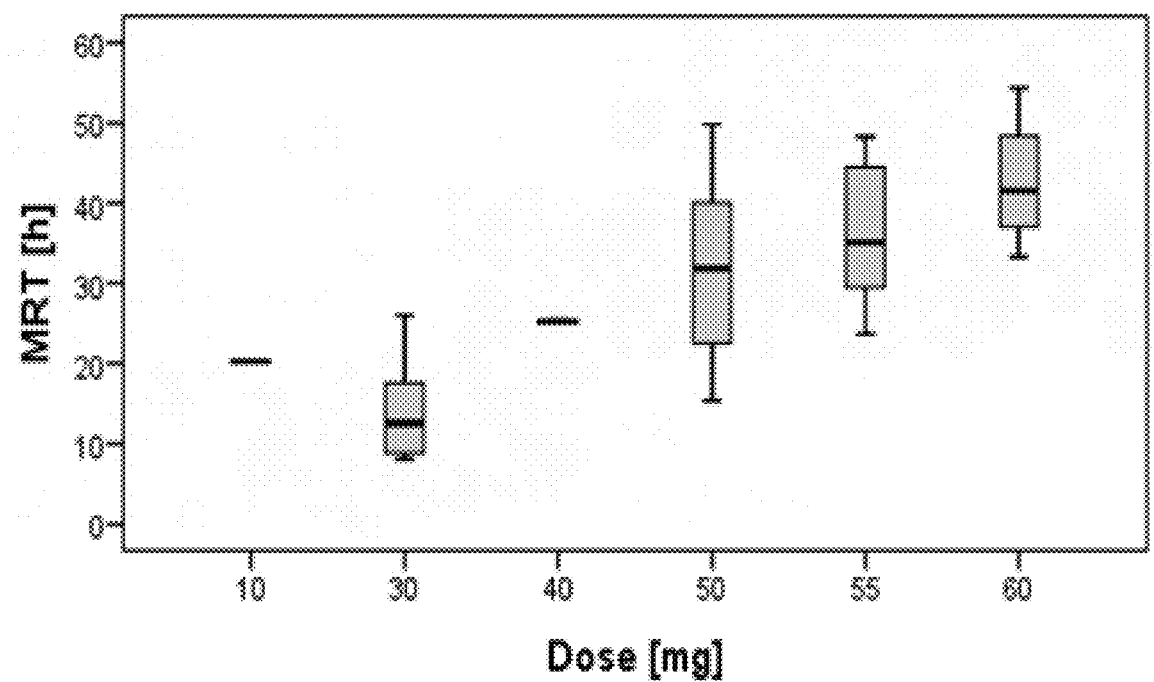
FIG. 2 shows the mean residence time of AV19-144 shows a dose-dependent increase ranging from 14.27 hours after 10 mg to 42.68 hours after 60 mg AV2-73.

This invention will be better understood with reference to the following definitions:

A. "Therapeutically effective amount" as to a drug dosage, shall mean that dosage that provides the specific pharmacological response for which the drug is administered in a significant number of subjects in need of such treatment. Here, the desired pharmacological response is a reduction in the number of seizures experienced by a subject. Seizures, their origin and management are subject to a variety of variables. Thus reference to "specific pharmacological response for which the drug is administered in a significant number of subjects in need of such treatment" is a recognition that a "therapeutically effective amount," administered to a particular subject in a particular instance will not abort every seizure onset, even though such dosage is deemed a "therapeutically effective amount" by those skilled in the art. It is to be further understood that drug dosages are, in particular instances, measured as oral dosages, or parenteral or inhaled dosages or with reference to drug levels as measured in blood.

A. Therapeutically effective amounts of A19-144 and A2-73 include 0.01-100 mg/daily, preferably 0.5-10 mg/daily, more preferably 0.5-2.0 mg/daily. Dosing once every two days (3 times a week) is noted.

B. "Co-timely" as to drug administration shall mean administration of a second drug while a first drug for is present in a therapeutically effective amount. It is to be understood that in some instances this will require sequential administration. In some instances, multiple routes of administration will be employed such as intravenous or subcutaneous injection.

C. "Coordinated" in the practice of the present invention of combining A19/2 administration with AED administration shall mean administration of at least one AED such that effective plasma levels of the AED will be present in a subject generally coincident with a therapeutically effective amount of A19/2. The coordination time is necessarily related to the route of AED administration. That is, for example, i.m. routes will generally have shorter lead times to peak plasma level than oral routes. In some embodiments this will be about 0.5 to about 12 hours after A19-144 or A2-73 has been administered.

D. "Unit dosage form" shall mean single drug administration entity. By way of example, a single tablet, capsule, dragee, or trochee, suppository, or syringe combining both A19-144 or A2-73 and at least one AED are examples of unit dosage forms.

E. "Enhanced therapeutic effect" in the context of this invention shall mean that relief from seizures (an increased latency period) with a disclose combination of A19-144 or A2-73 with at least one AED compared to the same doses of each component given alone; or that dose of one or both component(s) below what would otherwise be (apparently) a minimum effective dose (a "sub-MED").

F. As used herein, "prophylaxis" means complete absence of seizures or lessening of seizure frequency by at least 20% and preferably 50% and more preferably 80% as measured over the course of one year.

Without being bound by any particular theory it is believed that A19/2 act as a disease-modifying or pathology-modifying agents not only protecting brain cells from toxicity but also contributing to decrease Tau pathology and amyloid load. The pharmacokinetic data reveal a rapid and extensive biotransformation of AV2-73 to its main metabolite AV19-144 after oral administration.

Disclosed herein is the administration schedule and combination of A19-144 or A2-73 as a combination therapy with one or more AEDs.

A2-73 and metabolite AV19-144 were determined in plasma and urine using a validated high performance liquid chromatographic method (HPLC) with tandem mass spectrometry. After separation from human plasma analytes were injected into a LC-MS/MS. Quantification in plasma and urine was conducted by an internal standard method (AV2-73) and a peak area ratio method (AV19-144). A weighted (1/x) regression $2^{nd}$ order was performed to determine the concentration of the analytes. The study was conducted in accordance with the Principles of Good Laboratory Practice (GLP) as described under § 19, German Chemical Law. The validation based on the EG-Dok. CPMP/ICH/381/95 and was reported according to "FDA-Guidance for Industry, Bioanalytical Method Validation" (May 2001).

The impact of administration schedule and combination of A19-144A with donepezil or memantine is disclosed.

A19-144 was administered at 0.1 or 0.3 mg/kg ip once a day between day −7 and day −1 before $A\beta_{25-35}$ (day 0). It blocks the $A\beta_{25-35}$-induced memory deficits (spontaneous alternation in the Y maze and passive avoidance response) and lipid peroxidation in the hippocampus 7 days after $A\beta_{25-35}$. A19-144 (0.3 mg/kg ip) is also effective when administered once a day between day 7 and day 13 after $A\beta_{25-35}$ (on day 0), on memory deficits and lipid peroxidation increase measured 14 days after $A\beta_{25-35}$.

Both A19-144 and A2-73 are believed effective in preventing or moderating the peptide, $A\beta_{25-35}$,-induced toxicity and learning impairments when it is injected during one week before the peptide. Post-peptide administration is not required. Without being bound by any particular theory, this pre-insult protection schedule triggers neuromodulatory mechanisms (believed to impact the muscarinic and $\sigma_1$ receptors) to therapeutically protect the brain from amyloid toxicity. Chronic activation of the $\sigma_1$ receptor has been shown to facilitate ER stress response and modify lipid rafts composition, sustaining long-term modifications in the cell physiology.[7,8]

A19-144 is able to reverse the $A\beta_{25-35}$-induced toxicity and learning impairments when it is injected repeatedly one week after the peptide. This is a restorative effect of the compound, together with a delayed ability to reduce the toxic load in the brain. Without being bound by any particular theory, the protective pathways activated by muscarinic receptor (involving the PI3K/AKT and MAPK pathways), modulated by the $\sigma_1$ receptor activation are likely to be involved in these effects.

The anti-amnesic and neuroprotective effect of A19-144 and A2-73 against amyloid toxicity is effective in pre- and post-protection, meaning when the drug is administered before or after the amyloid peptide challenge, and the combination with donepezil boosts the therapeutic efficacy of each drug. A19-144 and A2-73 in combination with each of valproate, ethosuximide and gabapentin are also effective.

EXAMPLE 1

Seizure Prophylaxis: A19-144

A 13 year old male is experiencing 4 to 7 seizures per day with a baseline of 6.6 seizures per day. A19-144 is administered daily at 2.0 mg for 5 days. Seizures reduce to 2.2 per day for 8 weeks post dosing.

EXAMPLE 2

Seizure Prophylaxis: A19-144 and Donepezil

The 13 year old male of example 1 is experiencing seizures at 2.2 per day at 6 months post dosing as stated in Example 1. The subject is administered low dose donepezil (4 mg daily) for 5 days cotimely with continued A19-144 administration daily at 2.0 mg for 5 days. No seizures are detected at 6 months post dosing. Cognitive testing detects no diminution of memory as compared with the subject prior to donepezil administration.

EXAMPLE 3

Seizure Prophylaxis: A19-144

A 57 year old female is experiencing 6 to 8 seizures per day with a baseline of 6.6 seizures per day. A19-144 is administered daily at 2.0 mg for 5 days. Seizures reduce to 1.2 per day for 8 weeks post dosing.

EXAMPLE 4

Seizure Prophylaxis: A19-144 and Eslicarbazepine Acetate

The 57 year old female of Example 3 is experiencing an average of 1.2 seizures per day at 6 months post dosing as stated in Example 3. The subject is administered low dose Eslicarbazepine acetate at 600 mg/day; for 5 days cotimely with continued A19-144 administration daily at 2.0 mg for 5 days. No seizures are detected at 6 months post dosing. Cognitive testing detects no diminution of memory as compared with the subject prior to Eslicarbazepine acetate administration.

EXAMPLE 5

Seizure Prophylaxis: A19-144 and Lacosamide

A 10 year old female is experiencing seizures 3.2 per day. The subject is administered lacosamide at 60 mg two times per day for 5 days and cotimely administration of A19-144 daily at 2.0 mg for 5 days. No seizures are detected at 6 months post dosing.

EXAMPLE 6

Seizure Prophylaxis: A19-144 and Levetiracetam

The 9 year old female is experiencing an average of 3.3 seizures per day. The subject is administered Levetiracetam at 400 mg two times per day for 5 days and cotimely administration of 3.0 mg of A19-144 daily for 5 days. No seizures are detected at 6 months post dosing. Cognitive testing detects no diminution of memory as compared with the subject prior to Levetiracetam administration.

The results of Examples 1 through 6 above are similarly effective when A2-73 is substituted for A19-144.

Dosing Information/Dosage Forms:

For Anavex19-144and for A2-73, dosages of about .01-100 mg/daily, preferably 0.5-10 mg/daily, more preferably 0.5-2 mg/daily. Dosing once every two days (3 times a week) is noted. AD is a chronic disease, so staring treatment promptly with diagnosis is preferred. For dosages of donepezil, galantamine, rivastigmine, and memantinedonepezil, galantamine, rivastigmine is used advantageously in combination with A19-144 or with A2-73. In some embodiments, these may be administered in sub-MED doses.

Particular attention is drawn to the method of this invention comprising A19-144 and A2-73 administration combined with administration of at least one AED, wherein at least one of said therapeutically effective amounts of either A19-144 or A2-73 and the AED sub-therapeutic (sub-MED) as compared to the active dose when used alone. In the practice of this invention, either the A19/2 dose or the AED dose is used in sub-MED amount or both are. While this does not exclude more than one AED being used in treatment of a single subject, it is contemplated that particular embodiments will consist of A19-144 or A2-73 and an AED, wherein one or both drugs are administered in sub-MED amounts. Non-limiting useful doses for A19-144 or A2-73 in combination therapy are as follows:

Donepezil 1-3 mg/day or 5 mg once every two days; Rivastigmine 1 mg/day; Galantamine 8-10 mg/day once a day; and Memantine 1-5 mg/day.

Attention is drawn to dosages of donepezil of 5 mg or 10 mg administered orally once per day. Dosages up to about 23 mg/day are also noted.

Reported dosages of galantamine are about 8 to 16 mg twice daily. Note is made of dosage range from about 0.5 to about 8 mg, and optionally from about 1 to about 6 mg.

Reported rivastigamine dosages begin with about 1.5 mg orally twice a day with morning and evening meals. In some embodiments, after about two weeks of treatment, the rivastagmine dosage is increased to about 3 mg twice a day. Subsequent increases to 4.5 mg and 6 mg twice a day are noted. Rivastagmine is notably useful in transdermal patch form. A useful initial patch dose: 4.6 mg/24 hours, but a range of 1-8 mg is noted. In some embodiments a maintenance patch dose after about four weeks of treatment is increased from about 8-16 mg, and particularly, 9.5 mg/24 hours for as long as this dose is beneficial. The dose can then be increased to about 9-20 mg and particularly about 13.3 mg/24 hours.

Useful memantine dosing is initial about 5 mg orally once daily, then titrated upwards by 5 mg per week. Useful maintenance dosing is 5 mg once daily up to 10 mg twice daily are noted. Useful doses are from about 0.5 to about 20 mg, and lower (sub-MED) doses are contemplated.

Dosing for donepezil, galantamine, rivastigmine, or memantine may be daily, but further include from twice daily to every other day, to once per week or less frequently. Of course, transdermal dosing is also a continuous dosing.

The pharmacologically active compositions of this invention can be processed in accordance with conventional methods of Galenic pharmacy to produce medicinal agents for administration to subjects, e.g., mammals including humans.

The compositions of this invention individually or in combination are employed in admixture with conventional excipients, i.e., pharmaceutically acceptable organic or inorganic carrier substances suitable for parenteral, enteral (e.g., oral or inhalation) or topical application which do not deleteriously react with the active compositions. Suitable pharmaceutically acceptable carriers include but are not limited to water, salt solutions, alcohols, gum arabic, vegetable oils, benzyl alcohols, polyethylene glycols, gelatin, carbohydrates such as lactose, amylose or starch, magnesium stearate, talc, titanium dioxide, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compositions. They can also be combined where desired with other active agents, e.g., vitamins.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules, vials, and injector cartridges are convenient unit dosages.

Also for parenteral application, particularly suitable are tablets, dragees, liquids, drops, suppositories, or capsules. A syrup, elixir, or the like can be used wherein a sweetened vehicle is employed. Sublingual and buccal forms are also noted.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising A19-144 or A2-73 at about 1 to about 100 mg and 0.5 to 5 mg of donepezil or AED in a pharmaceutically acceptable carrier per unit dosage.

The invention claimed is:

1. A dosage form comprising a therapeutically effective amount of an active,
    wherein the active is
    (i) tetrahydro-N-methyl-2,2-diphenyl-3-furanomethanamine, or a pharmaceutically acceptable salt thereof;
    (ii) tetrahydro-N,N-dimethyl-2,2-diphenyl-3-furanomethanamine, or a pharmaceutically acceptable salt thereof; or
    a combination of (i) and (ii); and
    wherein the therapeutically effective amount is the amount to elicit pharmacological response of reduction in the daily number of seizures by at least 50%.

2. The dosage form of claim 1, wherein the therapeutically effective amount is 0.5-10 mg/day.

3. The dosage form of claim 1, wherein the dosage form further comprises a pharmaceutical excipient suitable for oral or parenteral administration.

4. The dosage form of claim 1, further comprising a sub-MED amount of at least one anti-epilepsy drug (AED).

5. The dosage form of claim 4, wherein the sub-MED amount of the at least one anti-epilepsy drug (AED) is selected from the group consisting of less than 5 mg/day of donepezil;
  less than 0.5 mg/day of memantine;
  less than 8 mg/day of galantamine;
  less than 3 mg/day of rivastigmine;
  less than about 8/day mg of acetazolamide;
  less than about 1.5 mg/day of Clonazepam for an adult, less than about 0.01 mg/kg/day of Clonazepam for a child up to 10 years of age or 30 kg of body weight;
  less than about 30 mg/day of Clorazepate;
  less than about 0.1 mg/kg/day of Lorazepam;
  less than about 0.2 mg/kg/day of Midazolam;
  less than about 7.5 mg/day of Carbamazepine;
  less than about 0.2 mg/kg/day of Diazepam;
  less than about 30 mg/day of Chlordiazepoxide;
  less than about 5 mg/day of Clobazam for body weight 30 kg or less, or less than about 10 mg/day of Clobazam for body weight 30 kg or more;
  less than about 5 mg/kg/day of Hydrocortisone;
  less than about 800 mg/day of Eslicarbazepine/Eslicarbazepine acetate;
  less than about 250 mg daily every 4-7 days of Ethosuximide;
  less than about 2 g daily of Ethotoin;
  less than about 1200 mg/day of Felbamate for adults or less than about 15 mg/kg/day of Felbamate for children 2-14 yrs;
  less than about 60 mg twice daily of Lacosamide;
  less than about 25 mg/day of Lamotrigine;
  less than about 1000 mg/day of Levetiracetam;
  less than about 200 mg/day of Mephyntoin;
  less than about 400 mg/day of Mephobarbitol;
  less than about 250 mg daily every 4-7 days of Methsuxamide;
  less than about 600 mg/day of Oxcarbazepine;
  less than about 150 mg/day of Paramethadione;
  less than about 2 mg/day of Perampanel (Fycompa);
  less than about 500 milligrams three times a day of Phenacemide;
  a Phenobarbital dose for reaching the serum level of less than about 10 pg/mL of Phenobarbital;
  less than about 0.5 g b.i.d of Phensuxamide;
  less than about 100 mg a day of Phenytoin;
  less than about 75 mg 2 times a day of Pregabalin;
  less than about 10 mg/kg/day of Primidone;
  less than about 2100 mg/day of Progabide;
  less than about 400 mg/day of Rufinamide;
  less than about 250 mg twice a day of Stiripentol;
  less than about 100 mg/day of Sulthiame;
  less than about 4 mg/day of Tiagabine;
  less than about 25 mg/day of Topiramate;
  less than about 900 mg/day of Tremethadione;
  less than about 10 mg/kg of Valproate;
  less than about 50 mg/kg/day of Vigabatrin;
  less than about 100 mg once a day of Zonisamide; and their combination thereof.

6. The dosage form of claim 5, wherein the dosage form is a unit dosage form.

7. A method of prophylaxis of seizures in a subject in need of such treatment comprising administering to the subject the dosage form of claim 1, wherein the method elicits reduction in the daily number of seizures by at least 50%.

8. The method of claim 7, wherein the subject is an epilepsy patient or a human being absent of a diagnosis of epilepsy.

9. The method of claim 7, wherein the subject is a pediatric patient.

10. The method of claim 7, wherein the dosage form is administered to the subject daily or once every two days.

11. The method of claim 7, wherein the method further comprises administering to the subject a sub-MED amount of at least one anti-epilepsy drug (AED).

12. The method of claim 11, wherein the administering of the at least one AED is co-timely with the administering of the active.

13. The method of claim 11, wherein the administering of the at least one AED is coordinated with the administering of the active.

14. The method of claim 11, wherein the subject does not experience diminution of memory post-AED administration as compared to pre-AED administration.

15. The method of claim 11, wherein the sub-MED amount of the at least one anti-epilepsy drug (AED) is selected from the group consisting of less than 5 mg/day of donepezil;
  less than 0.5 mg/day of memantine;
  less than 8 mg/day of galantamine;
  less than 3 mg/day of rivastigmine;
  less than about 8/day mg of acetazolamide;
  less than about 1.5 mg/day of Clonazepam for an adult, less than about 0.01 mg/kg/day for a child up to 10 years of age or 30 kg of body weight;
  less than about 30 mg/day of Clorazepate;
  less than about 0.1 mg/kg/day of Lorazepam;
  less than about 0.2 mg/kg/day of Midazolam;
  less than about 7.5 mg/day of Carbamazepine;
  less than about 0.2 mg/kg/day of Diazepam;
  less than about 30 mg/day of Chlordiazepoxide;
  less than about 5 mg/day of Clobazam for body weight 30 kg or less, or less than about 10 mg/day of Clobazam for body weight 30 kg or more;
  less than about 5 mg/kg/day of Hydrocortisone;
  less than about 800 mg/day of Eslicarbazepine/Eslicarbazepine acetate;
  less than about 250 mg daily every 4-7 days of Ethosuximide;
  less than about 2 g daily of Ethotoin;
  less than about 1200 mg/day of Felbamate for adults or less than about 15 mg/kg/day of Felbamate for children 2-14 yrs;
  less than about 60 mg twice daily of Lacosamide;
  less than about 25 mg/day of Lamotrigine;
  less than about 1000 mg/day of Levetiracetam;
  less than about 200 mg/day of Mephyntoin;
  less than about 400 mg/day of Mephobarbitol;
  less than about 250 mg daily every 4-7 days of Methsuxamide;
  less than about 600 mg/day of Oxcarbazepine;
  less than about 150 mg/day of Paramethadione;
  less than about 2 mg/day of Perampanel (Fycompa);
  less than about 500 milligrams three times a day of Phenacemide;
  a Phenobarbital dose for reaching the serum level of less than about 10 pg/mL of Phenobarbital;
  less than about 0.5 g b.i.d of Phensuxamide;

less than about 100 mg a day of Phenytoin;
less than about 75 mg 2 times a day of Pregabalin;
less than about 10 mg/kg/day of Primidone;
less than about 2100 mg/day of Progabide;
less than about 400 mg/day of Rufinamide;
less than about 250 mg twice a day of Stiripentol;
less than about 100 mg/day of Sulthiame;
less than about 4 mg/day of Tiagabine;
less than about 25 mg/day of Topiramate;
less than about 900 mg/day of Tremethadione;
less than about 10 mg/kg of Valproate;
less than about 50 mg/kg/day of Vigabatrin;
less than about 100 mg once a day of Zonisamide and their combination thereof.

16. A method of prophylaxis of seizures in a subject in need of such treatment comprising administering to the subject a low dose donepezil in conjunction with a therapeutic effective amount of tetrahydro-N-methyl-2,2-diphenyl-3-furanomethanamine, or a pharmaceutically acceptable salt thereof;

wherein the method elicits reduction in the daily number of seizures by at least 50%; and wherein the therapeutic effective amount is 0.5-10 mg/day.

17. The method of claim 16, wherein the low dose donepezil is administered co-timely at about 4 mg/day.

18. The method of claim 15, wherein the sub-MED amount of the at least one anti-epilepsy drug (AED) is eslicarbazepine acetate at daily sub-MED amount of about 600 mg/day.

19. The method of claim 15, wherein the sub-MED amount of the at least one anti-epilepsy drug (AED) is lacosamide at daily sub-MED amount of about 120 mg/day.

20. The method of claim 15, wherein the sub-MED amount of the at least one anti-epilepsy drug (AED) is levetiracetam at daily sub-MED amount of about 800 mg/day.

* * * * *